(12) United States Patent
Daniell

(10) Patent No.: US 10,689,633 B2
(45) Date of Patent: Jun. 23, 2020

(54) EXPRESSION OF β-MANNANASE IN CHLOROPLASTS AND ITS UTILIZATION IN LIGNOCELLULOSIC WOODY BIOMASS HYDROLYSIS

(71) Applicant: The Trustees of the University of Pennsylvania, Philadelphia, PA (US)

(72) Inventor: Henry Daniell, Winter Park, FL (US)

(73) Assignee: The Trustees of the University of Pennsylvania, Philadelphia, PA (US)

(*) Notice: Subject to any disclaimer, the term of this patent is extended or adjusted under 35 U.S.C. 154(b) by 200 days.

(21) Appl. No.: 13/659,396

(22) Filed: Oct. 24, 2012

(65) Prior Publication Data

US 2013/0137142 A1    May 30, 2013

Related U.S. Application Data

(63) Continuation-in-part of application No. 12/396,382, filed on Mar. 2, 2009.

(60) Provisional application No. 61/550,708, filed on Oct. 24, 2011, provisional application No. 61/032,536, filed on Feb. 29, 2008.

(51) Int. Cl.
    C12N 9/24     (2006.01)
    C12N 15/82    (2006.01)
    C12P 7/12     (2006.01)

(52) U.S. Cl.
    CPC ......... *C12N 9/2402* (2013.01); *C12N 9/2494* (2013.01); *C12N 15/8214* (2013.01); *C12N 15/8242* (2013.01); *C12N 15/8257* (2013.01); *C12P 7/12* (2013.01); *C12Y 302/01078* (2013.01)

(58) Field of Classification Search
    None
    See application file for complete search history.

(56) References Cited

U.S. PATENT DOCUMENTS

| | | | |
|---|---|---|---|
| 5,464,763 A * | 11/1995 | Schilperoort et al. | 800/294 |
| 5,693,507 A | 12/1997 | Daniell | |
| 5,877,402 A | 3/1999 | Maliga | |
| 5,932,479 A | 8/1999 | Daniell | |
| 6,326,470 B1 * | 12/2001 | Cosgrove | C07K 14/415 435/183 |
| 6,458,928 B1 * | 10/2002 | Swanson | C07K 14/37 435/262 |
| 6,642,053 B1 | 11/2003 | Daniell | |
| 6,680,426 B2 | 1/2004 | Daniell | |
| 7,129,391 B1 | 10/2006 | Daniell | |
| 7,135,620 B2 | 11/2006 | Daniell | |
| 7,294,506 B2 | 11/2007 | Daniell | |
| 7,354,760 B2 | 4/2008 | Daniell | |
| 7,462,762 B2 * | 12/2008 | Vidal | C12N 9/88 800/320.1 |
| 7,741,536 B2 | 6/2010 | Daniell | |
| 7,767,885 B2 | 8/2010 | Daniell | |
| 7,795,497 B2 | 9/2010 | Daniell | |
| 7,803,991 B2 | 9/2010 | Daniell | |
| 7,923,236 B2 * | 4/2011 | Gusakov | C11D 3/38645 162/174 |
| 8,344,205 B2 | 1/2013 | Daniell | |
| 8,481,810 B2 * | 7/2013 | Lebel et al. | 800/284 |
| 8,535,930 B2 | 9/2013 | Daniell | |
| 8,809,059 B2 | 8/2014 | Daniell | |
| 2002/0138878 A1 * | 9/2002 | Sticklen | C12N 15/8207 800/288 |
| 2002/0162135 A1 | 10/2002 | Daniell | |
| 2004/0177402 A1 | 9/2004 | Daniell | |
| 2005/0106699 A1 * | 5/2005 | Reddy et al. | 435/200 |
| 2005/0108792 A1 | 5/2005 | Daniell | |
| 2007/0124830 A1 | 5/2007 | Daniell | |
| 2008/0241916 A1 | 2/2008 | Daniell | |
| 2010/0304476 A1 | 2/2010 | Daniell | |
| 2010/0278869 A1 | 4/2010 | Daniell | |
| 2010/0266640 A1 | 10/2010 | Daniell | |
| 2010/0325756 A1 | 12/2010 | Daniell | |
| 2011/0072541 A1 | 3/2011 | Daniell | |
| 2011/0179530 A1 | 7/2011 | Daniell | |
| 2012/0135038 A1 | 5/2012 | Daniell | |

FOREIGN PATENT DOCUMENTS

| | | | |
|---|---|---|---|
| EP | 2260105 | 12/2010 | |
| EP | 2261364 | 12/2010 | |
| EP | 2284274 | 2/2011 | |
| WO | WO 9811235 A2 * | 3/1998 | C12N 15/8214 |

(Continued)

OTHER PUBLICATIONS

Xu et al (Journal of Biotechnology 131 (2007) 362-369.*
Malburg et al (Applied and Environmental Microbiology, Mar. 1996, p. 898-906) i.*
Gamauf et al (The Mycota, vol. IV: (2007) Environmental and Microbial Relationships, pp. 325-340).*
Zverlov et al (Microbiology (2002), 148, 247-255).*
Roy et al (Journal of Bacteriology, Jun. 1999, p. 3705-3709).*
Han et al (Enzyme and Microbial Technology 41 (2007) 638-645).*
Han et al (Enzyme and Microbial Technology 41 (2007) 638-645) (Year: 2007).*
Verma et al., "Chloroplast-derived enzyme cocktails hydrolyse lignocellulosic biomass and release fermentable sugars", Plant Biotechnology Journal, 8: 332-350 (2010).

(Continued)

*Primary Examiner* — Lee A Visone
(74) *Attorney, Agent, or Firm* — Kathleen D. Rigaut; Howson & Howson LLP

(57) ABSTRACT

Disclosed herein are materials useful for degrading plant biomass material. In exemplary embodiments, the plant material comprises one or more enzymes that are expressed in plants and/or bacteria. Specifically exemplified herein are plant degrading enzymes expressed in chloroplasts. The chloroplast expressed enzymes may be provided as cocktails for use in conjunction with conventional methods of converting biomass into biofuels, such as cellulosic ethanol. In other exemplary embodiments, methods and materials are disclosed for degrading mannans.

6 Claims, 4 Drawing Sheets
Specification includes a Sequence Listing.

(56) References Cited

FOREIGN PATENT DOCUMENTS

| WO | 99/10531 | 3/1999 | | |
|---|---|---|---|---|
| WO | 1999010513 | 3/1999 | | |
| WO | 99/18225 | 4/1999 | | |
| WO | 00/03012 | 1/2000 | | |
| WO | 2001064850 | 9/2001 | | |
| WO | 2001064927 | 9/2001 | | |
| WO | 2001064929 | 9/2001 | | |
| WO | 2001072959 | 10/2001 | | |
| WO | 2003057834 | 7/2003 | | |
| WO | 2004005467 | 1/2004 | | |
| WO | 2004005480 | 1/2004 | | |
| WO | 2004005521 | 1/2004 | | |
| WO | 2006027865 | 3/2006 | | |
| WO | 2007053183 | 10/2007 | | |
| WO | WO 2007115723 A3 * | 11/2007 | ......... | A23L 1/3055 |
| WO | 2008121947 | 10/2008 | | |
| WO | 2008121953 | 10/2008 | | |
| WO | 2009058355 | 5/2009 | | |
| WO | 2010033275 | 3/2010 | | |
| WO | 2011057243 | 5/2011 | | |

OTHER PUBLICATIONS

Yang et al., "Enzymatic hydrolysis of cellulosic biomass", Biofuels, 2(4): 421-450 (2011).
Sijmons et al., Production of Correctly Processed Human Serum Albumin in Transgenic Plants, Biotechnology,1990, 217-221, 8.
Staub et al., Long regions of homologous DNA are incorporated into the tobacco plastid genome by transformation. Plant Cell,1992, 39-45, 4(1).
Kanno, A Transcription Map of the Chloroplast Genome from Rice (*Oryza sativa*), Curr Genet., 1993, 166-174, 23, 2.
Zoubenko et al., Efficient Targeting of Foreign Genes into the Tobacco Plastid Genome, Nucleic Acid Research, 1994, 3819-1824, 22(19).
McBride et al., Amplification of a Chimeric Bacillus Gene in Chloroplasts Leads to an Extraordinary Level of an insecticidal Protein in Tobacco, Nature Biotechnology,1995, 362-365, 13.
Boston et al., Molecular Chaperones and Protein Folding in Plants, Plant Molecular Biology, 1996, 191-222, 32.
Lu et al., Characterization of Republication Origins Flanking the 23S rRNA Gene in Tobacco Chloroplast DNA, Plant Mol. Biol., 1996, 693-706, 32.
Daniell, Containment of Herbicide Resistance Through Genetic Engineering of the Chloroplast Genome, Nature Biotechnology, 1998, 345-348, 16.
Crickmore et al., Revision of the Nomenclature for the Bacillus thuringiensis Pesticidal Crystal Proteins, Microbiology and Molecular Biology Reviews, 1998, 807-813, 62.
Kota et al., Overexpression of Bacillus thuringiensis (Bt) Cry2Aa2 Protein in Chloroplast Confers Resistance to Plants Against Susceptible and BI-resistant Insects, Proc. Natl. Acad. Sci. USA, 1999, 1840-1845, 96.
Heifetz, Genetic Engineering of the Chloroplast, Biochimie, 2000, 655-666, 82.
Daniell et al., Multigene engineering: dawn of an exciting new era in biotechnology, Curr Opin Biotechnol., 2002, 136-41, 13(2).
Daniell et al., Milestones in chloroplast genetic engineering: an environmentally friendly era in biotechnology, Trends Plant Sci., 2002, 84-91, 7(2).
Leelavathi et al., Chloroplast expression of His-tagged GUS-fusions: a general strategy to overproduce and purify foreign proteins using transplasmotic plants as bioreactors, Molecular Breeding, 2003, 49-58, 11.
Watson et al., Expression of Bacillus anthracis protective antigen in transgenic chloroplasts of tobacco, a non-food/feed crop, Vaccine, 2004, 4374-84, 22(31-32).

Kumar et al., Plastid-expressed betaine aldehyde dehydrogenase gene in carrot cultured cells, roots, and leaves confers enhanced salt tolerance, Plant Physiol., 2004, 2843-54, 136(1).

Kumar et al., Stable transformation of the cotton plastid genome and maternal inheritance of transgenes, Plant Mol Biol., 2004, 203-16, 56(2).

Lelivelt et al., Stable plastid transformation in lettuce (*Lactuca sativa* L.), Plant Mol Biol., 2005, 763-774, 58.

Quesada-Vargas et al., Characterization of heterologous multigene operons in transgenic chloroplasts: transcription, processing, and translation, Plant Physiol., 2005, 1746-62, 138(3).

Koya et al., Plant-based vaccine: mice immunized with chloroplast-derived anthrax protective antigen survive anthrax lethal toxin challenge, Infect Immun., 2005, 8266-74, 73(12).

Daniell et al., Breakthrough in chloroplast genetic engineering of agronomically important crops, Trends Biotechnol., 2005, 238-45, 23(5).

Limaye et al., Receptor-mediated oral delivery of a bioencapsulated green fluorescent protein expressed in transgenic chloroplasts into the mouse circulatory system, FASEB J., 2006, 959-61, 20(7).

Lee et al., Plastid transformation in the monocotyledonous cereal crop, rice (*Oryza sativa*) and transmission of transgenes to their progeny, Mol Cells., 2006, 401-10, 21(3).

Daniell et al., Chloroplast genetic engineering, Biotechnol J., 2006, 26-33, 1(1).

Verma et al., Chloroplast vector systems for biotechnology applications, Plant Physiol., 2007, 1129-43, 145(4).

Ruhlman et al., Expression of cholera toxin B-proinsulin fusion protein in lettuce and tobacco chloroplasts—oral administration protects against development of insulitis in non-obese diabetic mice, Plant Biotechnol J., 2007, 495-510, 5(4).

Daniell et al., Transgene containment by maternal inheritance: effective or elusive? Proc Natl Acad Sci U S A, 2007, 6879-80, 104(17).

Chebolu et al., Stable expression of Gal/GalNAG lectin of Entamoeba histolytica in transgenic chloroplasts and immunogenicity in mice towards vaccine development for amoebiasis, Plant Biotechnol J., 2007, 230-9, 5(2).

Daniell et al., The complete nucleotide sequence of the cassava (*Manihot esculenta*) chloroplast genome and the evolution of atpF in Malpighiales: RNA editing and multiple losses of a group II intron, Theor Appl Genet., 2008, 723-37, 116(5).

Arlen et al., Effective plague vaccination via oral delivery of plant cells expressing F1-V antigens in chloroplasts, Infect Immun., 2008, 3640-50, 76(8).

Davoodi-Semiromi et al., The green vaccine: A global strategy to combat infectious and autoimmune diseases, Hum Vaccin., 2009, 488-93, 5(7).

Daniell et al., Plant-made vaccine antigens and biopharmaceuticals, Trends Plant Sci., 2009, 669-79, 14(12).

Verma et al., Oral delivery of bioencapsulated coagulation factor IX prevents inhibitor formation and fatal anaphylaxis in hemophilia B mice, Proc Natl Acad Sci U S A, 2010, 7101-6, 107(15).

Verma et al., Chloroplast-derived enzyme cocktails hydrolyse lignocellulosic biomass and release fermentable sugars, Plant Biotechnol J., 2010, 332-50, 8(3).

Ruhlman et al., The role of heterologous chloroplast sequence elements in transgene integration and expression, Plant Physiol., 2010, 2088-104, 152(4).

Davoodi-Semiromi et al., Chloroplast-derived vaccine antigens confer dual immunity against cholera and malaria by oral or injectable delivery, Plant Biotechnol J., 2010, 223-42, 8(2).

Lee et al., Expression and characterization of antimicrobial peptides Retrocyclin-101 and Protegrin-1 in chloroplasts to control viral and bacterial infections, Plant Biotechnol J., 2011, 100-15, 9(1).

Boyhan et al., Low-cost production of proinsulin in tobacco and lettuce chloroplasts for injectable or oral delivery of functional insulin and C-peptide, Plant Biotechnol J., 2011, 585-98, 9(5).

Clarke et al., Plastid biotechnology for crop production: present status and future perspectives, Plant Mol Biol., 2011, 211-20, 76(3-5).

Arakawa et al., A Plant-based cholera toxin B subunit-insulin fusion protein protects against the development of autoimmune disease, Nature Biotechnology, 1998, 934-938, vol. 16.

(56) References Cited

OTHER PUBLICATIONS

Degray et al., Expression of an Antimicrobial Peptide via the Chloroplast Genome to Control Phytogenic Bacteria and Fungi, Plant Physiology, 2001, 852-862, vol. 127.

Ademark et al., Softwood hemicellulose-degrading enzymes from Aspergillus niger: Purification and properties of a B-mannanase, Journal of Biotechnology, 1998, 199-210, vol. 63.

Banerjee et al., Rapid optimization of enzyme mixtures for deconstruction of diverse pretreatment/biomass feedstock combinations, Biotechnology for Biofuels, 3: 22 (2010).

Dhawan et al., "Microbial Mannanases: An Overview of Production and Applications", Critical Review in Biotechnology, 27: 197-216 (2007).

Jorgensen et al., "Production of Ethanol and Feed by High Dry Matter Hydrolysis and Fermentation of Palm Kernel Press Cake", Appl. Biochem. Biotechnol., 161: 318-332 (2010).

Moreira et al., "An overview of mannan structure and mannan-degrading enzyme systems", Appl. Microbiol. Biotechnol., 79: 165-178 (2008).

Petersen et al., "High-level expression of a suite of thermostable cell wall-degrading enzymes from the chloroplast genome", Plant Mol. Biol., 76: 311-321 (2011).

Pham et al., "Hydrolysis of softwood by Aspergillus mannanase: Role of a carbohydrate-binding module", Journal of Biotechnology, 148: 163-170 (2010).

Sticklen et al., "Plant genetic engineering to improve biomass characteristics for biofuels", Current Opinion in Biotechnology, 17: 315-319 (2006).

\* cited by examiner

EXPRESSION OF β-MANNANASE IN CHLOROPLASTS AND ITS UTILIZATION IN LIGNOCELLULOSIC WOODY BIOMASS HYDROLYSIS

CROSS-REFERENCE TO RELATED APPLICATIONS

This application is a continuation in part application to U.S. application Ser. No. 12/396,382, filed Mar. 2, 2009, which is related to and claims priority to U.S. Provisional Application No. 61/032,536 filed Feb. 28, 2008. This application is also related to U.S. Provisional Application No. 61/550,708 filed Oct. 24, 2011. Priority to the foregoing applications is claimed under 35 USC 119, 120, and are incorporated in their entirety by reference.

STATEMENT OF FEDERALLY FUNDED RESEARCH

This invention was made with government support under grant no. 2010-39200-21704 awarded by the United States Department of Agriculture/National Institute of Food and Agriculture; under grant no. 2009-39200-19972 awarded by the United States Department of Agriculture/National Institute of Food and Agriculture; and under grant no. R01 GM063879 awarded by the National Institute of Health. The government has certain rights in the invention.

SEQUENCE LISTING

The instant application contains a Sequence Listing which has been submitted in ASCII format via EFS-Web and is hereby incorporated by reference in its entirety. Said ASCII copy, created on Jan. 18, 2013, is named 10669136.txt and is 1,091 bytes in size.

BACKGROUND

The world's energy demands are ever increasing and cannot be sustained by conventional fuel sources alone. Therefore, biofuels are needed as an alternative source of energy. The current production of fuel grade ethanol utilizes food crops such as corn grain, which consumes about 25% of U.S corn production and therefore competes with food source [1,2, the world wide web at 1.eere.energy.gov/biomass/pdfs/us_biofuels_industry_report.pdf]. Lignocellulosic biomass is a renewable alternative source for bioethanol production, which includes agricultural wastes such as pinewood, citrus peel, corn stover, poplar waste, bagasse and rice straw. Currently, large amount of these biomass feed stocks are available for their conversion to fermentable sugars for bioethanol production (United States Department of Energy, on the world wide web at 1.eere.energy.gov/biomass/feedstock_databases.html). Lignocellulosic biomass is rich in cellulose and hemicellulose which are difficult to breakdown into fermentable sugars due to the complex structure of the cell wall. For breakdown of complex biomass, chemical and physical pretreatments of these materials are necessary. These treatments are expensive, have serious environmental consequences and impact enzymatic hydrolysis [3]. To reduce such environmental effects of pretreatments, a cost effective and environmentally friendly solution should be considered. As the cellulosic biomass is composed of complex cellulose, hemicellulose and various entangled fibers, concurrent action of different enzyme classes such as cellulases, glucosidases, hemicellulases and accessory enzymes including esterases, lipases, pectate lyases etc. are required, in large quantities [3]. Simultaneous action of these enzymes can increase the access of each enzyme to the cellulosic biomass.

DETAILED DESCRIPTION

Figure 1:
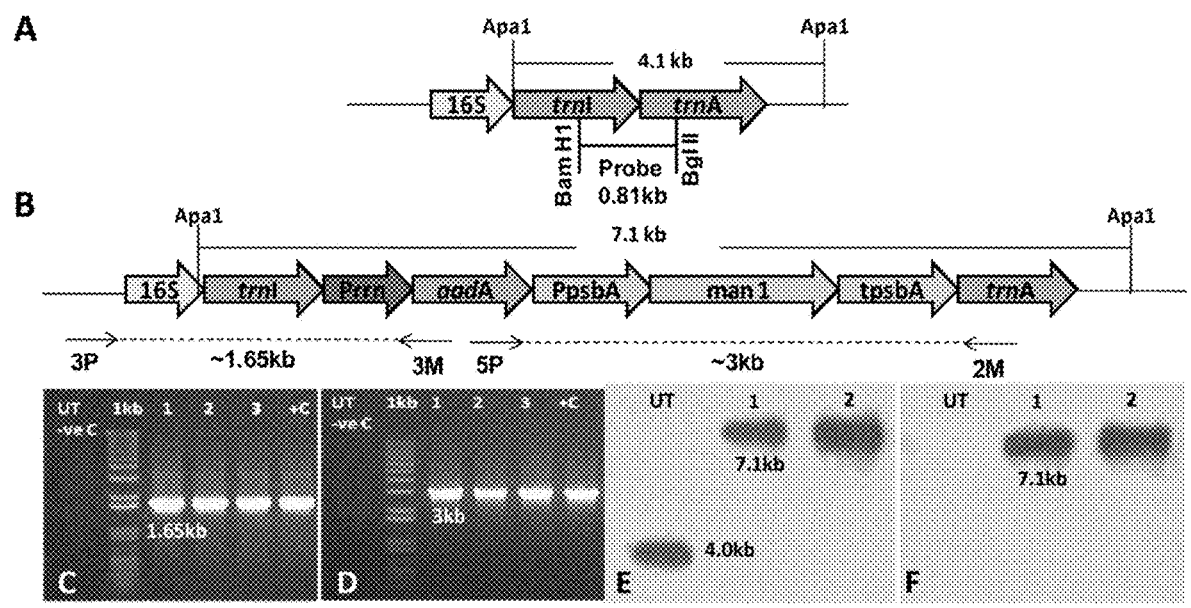
FIG. 1 Characterization of transplastomic plants. A & B, Schematic representation of chloroplast flanking sequences used for homologous recombination, probe DNA sequence (0.81 kb), primer annealing sites (3P/3M and 5P/2M) and expected products of untransformed and transgenic lines when digested with Apa I. Prrn, rRNA operon promoter; aadA, aminoglycoside 3 adenylyltransferase gene; PpsbA, promoter and 5' untranslated region of the psbA gene; tpsbA, 3' untranslated region of the psbA gene. C, PCR analysis using primer pairs 3P/3M and D, 5P/2M. Lane1-3, transplastomic lines; UT, Untransformed (-ve C); +C, positive control for 3P/3M confirmed established transplastomic line, for 5P/2M pLD man1; 1 kb, 1 kb plus DNA ladder. E, Southern blot hybridized with the flanking sequence probe. Lanes 1-2, transplastomic lines; UT, Untransformed. F, Southern blot hybridized with man1 probe. Lanes 1-2, transplastomic lines; UT, Untransformed.

Heterologous expression of both fungal and bacterial mannanase has been used for the production of enzyme via submerged fermentation. Because of the need for prohibitively expensive infrastructure for prevention of contamination by other microbes, high production cost and limited capability of fermentation facilities for producing various biomass hydrolyzing enzymes, disclosed herein are methods and materials of planta expression of these enzymes.

Hemicelluloses are complex polysaccharides present in plant cell wall and mannans are important constituents of hemicellulosic fraction, which are abundantly present as glucomannan or galactoglucomannan in the wood of gymnosperm plants [4]. Wood dry mass contains 20-25% of galactoglucomannan and is the main component of softwood hemicellulose. It is composed of a linear chain of D-mannopyranose and D-glucopyranose units linked by β-(1, 4) glycosidic bonds. The glucose and mannose in the linear chain are partially substituted by α-D-galactopyranosyl units via α-(1, 6) bonds. On the other hand glucomannans constitutes approximately 5% of the secondary cell wall of hardwood [5, 6]. Lignocellulosic biomass rich in mannans include softwood from gymnosperms such as pinewood (10%), poplar wood (4%), and cellulose sludge (4%) (United States Department of Energy, on the world wide web at 1.eere.energy.gov/biomass/feedstock_databases.html). Algae including *Acetabularia* and *Porphyra* contain up to 20% mannans in their cell wall [7, 8] which can be utilized for ethanol production [9]. Algae are also important producers of biodiesel, after the lipids are extracted for biodiesel production; the remaining waste is rich in carbohydrates and can be used as a substrate for bioethanol production [9].

Endo β mannanase (3.2.1.78) belongs to glycoside hydrolase enzyme family 5, which randomly cleaves β-D-1,4-mannopyranosyl linkage in the main chain of mannans and heteromannans including galactomannans, glucomannans and galactoglucomannans. The main hydrolysis products obtained by the action of endo β mannanase are mannobiose and mannotriose [10-12]. Mannanases have diverse industrial applications including bleaching of the softwood pulp in paper industry, reducing the viscosity of coffee extracts rich in mannans, oil extraction of coconut meat, oil and gas well stimulation, as a stain removal agent in detergents, neutraceutical and excipient production in the pharmaceutical industry [10,12]. Recently, mannanases have gained importance for their role in hydrolysis of the hemicellulose fraction in the lignocellulosic biomass for efficient breakdown of the complex polysaccharides into simple sugars for bioethanol production [13]. Endo β mannanase is one among the most important hemicellulases for hydrolysis of lignocellulosic biomass. Analysis of a range of enzyme combinations on palm kernel press cake (PKC) showed that including cellulases in combination with mannanase significantly improved ethanol yields up to 70 g/kg of PKC [13]. An optimal enzyme cocktail for the hydrolysis of AFEX (ammonia fiber expansion) treated DDGS (dried distillers grains with solubles) has been reported to contain high amount of mannanase. As DDGS consists of 2.5% mannans, including excess of mannanase resulted in the efficient hydrolysis of DDGS and thereby increasing glucose yields [14]. Another study demonstrated that adding chimeric *Aspergillus niger* mannanase to the hydrolysis enzyme cocktail of *Trichoderma reesei* enzyme improved hydrolysis of lignocellulosic substrate softwood [6].

Several organisms including bacteria, actinomycetes, yeast and fungi have been reported to hydrolyze mannans. Among bacteria, *Bacillus* is the most established mannanase producing group and has been extensively studied [10, 15]. The most utilized fungus in the industrial production of mannanase with immense capability to act on a variety of mannan substrates belongs to genera *Trichoderma* and *Aspergillus* [10,16,17]. *Trichoderma reesei* is a filamentous fungus which produces industrially important cellulases and hemicellulases. Endo β mannanase from *Trichoderma reesei* has been isolated, purified and characterized [16, 18, 19]. The three dimensional structure of *Trichoderma reesei* mannanase has been elucidated and reveals the presence of four disulfide bonds. Further, additional substrate binding subsites were discovered which are absent in the bacterial enzyme [20]. In another study, *Trichoderma reesei* mannanase successfully hydrolyzed galactomannan in pine kraft pulp, whereas mannanase from *Bacillus subtilis* was not able to do so [21-23]. Sequence alignment and hydrophobic cluster analysis have shown that mannanase from *T. reesei* consists of two modules. One is the N-terminal catalytic module and another is a C-terminal carbohydrate binding module (CBM) [19, 24]. CBM brings the enzyme in close vicinity of the polysaccharide substrate and hence increases the concentration of enzyme at the substrate [25]. A *Trichoderma reesei* mannanase mutant lacking the CBM showed five-fold less hydrolysis of ivory nut mannan when compared to mannanase with CBM [24].

In planta expression of cell wall degrading enzymes has benefits over other heterologous production systems including remarkable ability for scale up, well established large scale production and harvesting methods, increased enzyme yield/stability and various storage alternatives [26,27]. Tobacco is a suitable host for in planta production of cell wall degrading enzymes because it produces large amount of biomass. The commercial tobacco cultivars yield up to 40 metric tons of biomass per year in three harvests [28]. Advantages of expressing biomass hydrolyzing enzymes via the chloroplast genome include high levels of expression due to thousands of copies of transgenes in each cell, containment of transgenes via maternal inheritance and minimal pleiotropic effects due to compartmentalization of enzymes within chloroplasts, away from the cell wall.

There are reports that have investigated the heterologous production of biomass degrading enzymes in plants via nuclear transformation [29, 30]. Production of enzymes through nuclear transformation has several limitations including low expression levels, gene silencing and position effect [31]. Plastid transformation has shown the ability to produce significant amounts of certain foreign proteins (up to 72% levels of total leaf protein) [32, 33]. Engineering foreign genes in the chloroplast genome may provide containment from pollen transmission as organelle genes are maternally inherited in most crops [34]. In addition, harvesting leaves before flowering provides nearly complete transgene containment [31, 34]. Transgene integration into the chloroplast genome occurs by site specific homologous recombination; therefore this can sometimes avoid gene silencing or position effects [31].

It is shown herein that proper protein folding and disulfide bond formation may occur in chloroplasts [35-38]. Also, it has been suggested that compartmentalization within chloroplasts may minimize negative pleiotropic effects of cell wall hydrolyzing enzymes [39] or even increases biomass [40]. However, other reports have shown that expression of biomass degrading enzyme had drastic phenotypic effect on the transplastomic plants [41].

A chloroplast-derived enzyme cocktail has been formulated for the hydrolysis of lignocellulosic biomass based on its composition [42] but did not contain mannanase which is an integral part of an enzyme cocktail for biomass hydrolysis [14]. Woody biomass including pinewood and algal biomass consists of significant amount of mannans. Therefore, as disclosed herein man1 gene from *Trichoderma reesei* was expressed into tobacco chloroplasts. The chloroplast-derived mannanase was characterized and used to formulate an enzyme cocktail for pinewood hydrolysis. Use of mannanase in enzyme cocktail released 20% more fermentable sugars from pinewood than the cocktail without mannanase. To our knowledge, this is the first report of expression of fungal mannanase in plants and their direct utilization in enzyme cocktails, without any need of purification for lignocellulosic biomass hydrolysis.

According to a first embodiment, a method is disclosed herein that includes degrading a plant biomass sample so as to release fermentable sugars therein. The method includes obtaining a plant degrading cocktail comprising at least one cell extract, the cell extract comprising an active plant degrading compound recombinantly expressed in cells from which said cell extract is derived, and wherein the at least one cell extract comprising β-Mannanase. The method embodiment also involves admixing the plant degrading cocktail with said biomass sample. In a specific embodiment, the method involves at least two cell extracts, wherein the at least two cell extracts include the plant cell extract comprising a first plant degrading compound, β-Mannanase, and at least one other cell extract comprising a second plant degrading compound.

Further to the first embodiment, a method is disclosed wherein the at least two cell extracts are provided in a plant degrading cocktail, and the second plant degrading compound includes cellulase, ligninase, beta-glucosidase, hemicellulase, xylanase, alpha amylase, amyloglucosidase, pectate lyase, cutinase, lipase, maltogenic alpha-amylase, pectolyase or expansin.

In alternative embodiments, methods are provided that include rubisco in the plant degrading cocktail. In addition, and alternatively, plant degrading cocktails are provided that include at least one chloroplast genome or genome segment having a heterologous gene that encodes β-Mannanase; and wherein the plant cell extract comprises β-Mannanase Compositions, extracts and cocktails disclosed herein may be used to degrade plant biomass sample, including grain and/or grain residues, sugar beet, sugar cane, grasses, wood-based biomass, fruits and/or fruit waste residues, or a combination thereof. In a specific embodiment, the plant biomass is corn, wheat, barley, or citrus, or waste residues obtained therefrom. According to another embodiment, the plant biomass is: switchgrass, or sawdust or otherwise processed wood; or sugar cane; or citrus peel; or sugar beet. According to a typical embodiment, the biomass is woody-based plant biomass.

According to another embodiment, a plant-degrading cocktail is provided that is useful for degrading a plant biomass. The cocktail comprises at least two recombinantly expressed plant degrading enzymes and rubisco, and optionally, expansin. In a specific embodiment, the two plant degrading enzymes included in the cocktail include a combination of the following enzymes: β-Mannanase, cellulase, ligninase, beta glucosidase, hemicellulase, xylanase, alpha-amylase, amyloglucosidase, pectate lyase, cutinase, lipase, pectolyase, or maltogenic alpha amylase.

Another method embodiment is provided, wherein said at least one cell extract is produced by producing a first plant comprising chloroplasts that express a first plant degrading enzyme, e.g. β-Mannanase; harvesting said first plant; and processing said first plant to produce an enzyme source comprising β-Mannanase suitable for mixing with and degrading a biomass sample. The plant may be multiple suitable plant species. In a specific embodiment, the plant is tobacco. In a specific embodiment, the processing step comprises homogenizing said first plant or a portion thereof.

In a more specific aspect, a method is provided wherein the producing step comprises at least two of the following: producing a first plant comprising chloroplasts that express β-Mannanase, producing a second plant comprising chloroplasts that express lignanase, producing a third plant comprising chloroplasts that express beta-glucosidase; producing a fourth plant comprising chloroplasts that express hemicellulase; producing a fifth plant comprising chloroplasts that express xylanase; producing a sixth plant comprising chloroplasts that express alpha-amylase; producing a seventh plant comprising chloroplasts that express amyloglucosidase; producing an eighth plant comprising chloroplasts that express pectate lyase; producing a ninth plant comprising chloroplasts that express cutinase; producing a tenth plant comprising chloroplasts that express lipase; producing an eleventh plant comprising chloroplasts that express maltogenic alpha amylase, producing a twelfth plant comprising chloroplasts that express pectolyase or a thirteenth plant comprising chloroplasts that express expansin (e.g. swollenin).

Compositions, extracts and/or cocktails may be in a solid form, liquid form or semi-liquid form.

In a specific embodiment, a plant degrading enzyme cocktail useful in digesting a wood-based biomass sample is provided. The cocktail may include plant expressed β-Mannanase, and optionally, in addition, cellulase, beta-glucosidase, xylanase, alpha amylase, amyloglucosidase, pectin lyase, swollenin and pectate lyase, and/or an amount of rubisco.

A method of producing a plant biomass degrading material is provided that includes producing at least one plant comprising chloroplasts that express β-Mannanase, harvesting said plant; and processing said plant to produce plant degrading material suitable for mixing with and degrading a biomass sample.

Examples discussed below teach the expression of mannanase in tobacco, but those skilled in the art will appreciate that, in view of the teachings herein, chloroplasts from other species can be transformed to produce mannanase as well. Other plants that may be transformed to produce mannanase or other enzymes discussed herein include but are not limited to, maize, rice, grass, rye, barley, oat, wheat, soybean, peanut, grape, potato, sweet potato, pea, canola, tobacco, tomato, lettuce, carrot, melon, or cotton.

EXAMPLES

Construction of Chloroplast Transformation Vector Harboring man1 Gene

Coding sequence of man1 gene (three exons) was amplified by PCR [43] from *Trichoderma reesei* genomic DNA. Agarose gel analysis of the final PCR product showed a product of 1338 bp, which was cloned in pCR Blunt II Topo vector (Invitrogen) and sequence was verified. Tobacco chloroplast transformation vector pLD-man1 (FIG. 1B) was constructed with man1 coding sequence based on the universal chloroplast vector that targets the transgene expression cassette into the transcriptionally active spacer region between the trnI and trnA genes (FIG. 1A) of the chloroplast genome for integration via homologous recombination [44]. The man1 gene was driven by light and developmentally regulated psbA promoter and 5' UTR, which contains several ribosome binding sites to enhance transgene expression levels [28]. The 3' UTR located at the 3' end of man1 coding sequence stabilized the transcript. The aadA gene conferring spectinomycin resistance for selection of transformants was driven by the constitutive tobacco plastid ribosomal operon promoter (Prrn).

Evaluation of Site Specific Integration and Homoplasmy of Transplastomic Plants

Transplastomic mannanase plants were regenerated as described previously [45]. Six independent shoots (per 10 bombardments) appeared from the leaves placed on the regeneration medium containing spectinomycin within 3-6 weeks after bombardments with pLD-man1 plasmid DNA coated on gold particles. PCR analysis using 3P/3M validated the site specific integration of the transgenes into the tobacco chloroplast genome. The 3P primer lands on the native chloroplast genome within the 16S rRNA gene upstream of the gene cassette and 3M primer lands on the aadA gene which is located within the gene cassette (FIG. 1B). PCR reaction with 3P/3M primers generated a 1.65 kb PCR product in transplastomic lines (FIG. 10, Lanes: 1-3), which should be obtained only if site specific integration had occurred. Nuclear transformants, mutants and untransformed plants did not show any PCR product as 3P or 3M primer will not anneal (FIG. 10, Lane: UT). The integration of aadA and man1 genes was verified by using 5P and 2M primer pair for PCR analysis. These primers anneal at different locations within the transgene cassette. The 5P primer anneals to the aadA gene whereas 2M primer anneals to the trnA coding sequence (FIG. 1B). The use of 5P/2M primer pair produced a PCR product of ~3 kb in the transplastomic lines and positive control (pLD-man1) whereas untransformed plant did not show any product (FIG. 1D). After PCR analysis, transplastomic plants were moved to additional two rounds of selection (second and third) to achieve homoplasmy.

Southern blot analysis was performed to determine homoplasmy and to further confirm the site specific integration. The flanking sequence probe (0.81 kb, FIG. 1A), which hybridizes with the trnI and trnA genes allowed determination of homoplasmy or heteroplasmy and site specific integration of the transgene cassette into the chloroplast genome. Hybridization of nylon membrane with flanking sequence probe produced fragments of 7.1 kb in transplastomic lines (FIG. 1E, Lane 1 & 2) and 4.0 kb (FIG. 1E, Lane UT) in untransformed plant. Absence of 4 kb fragment in transplastomic lines confirmed homoplasmy (within the detection limits of Southern blot) and stable integration of foreign genes into the chloroplast genome, whereas the detection of 4 kb fragment in untransformed plants confirmed that these plants lacked foreign genes. In addition, the man1 probe was utilized to verify the presence of man1 gene, which produced a 7.1 kb fragment in transplastomic lines (FIG. 1F, Lanes 1 & 2). No hybridizing fragment was observed in the untransformed line confirming the absence of the man1 gene (FIG. 1F, Lane UT).

Phenotypic Evaluation of Mannanase Plants

Figure 2:
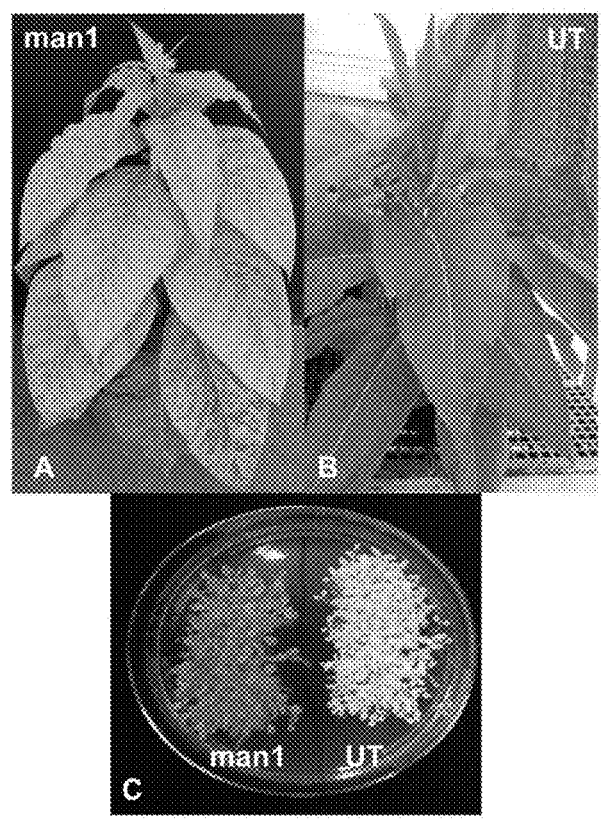
FIG. 2 Phenotype of transplastomic mannanase plants. A, Mannanase transplastomic plant growing autotrophically in the green house. Mannanase plants were fertile and set seeds. B, Untransformed (UT) plant C, Transplastomic (man1) seeds and Untransformed (UT) seeds germinated on MSO medium containing spectinomycin (500 mg/L) showing lack of Mendelian segregation.

Homoplasmic lines were transferred to Jiffy pellets and were kept in high humid conditions for 2 weeks before being transferred to the green house to grow under autotrophic conditions. Mannanase transplastomic plants showed mild phenotypic effects in green house with some leaves turning pale as they matured. In spite of this, transplastomic plants grew normally, flowered, set seeds and produced biomass similar to untransformed plants (FIG. 2A, 2B). Mannanase T1 seeds were germinated along with untransformed seeds on spectinomycin (500 mg/l) selection medium. Mannanase seedlings remained green whereas untransformed seeds turned white (FIG. 2C). These results, observed among several hundred seedlings (only one representative plate shown in FIG. 2C), indicate that the transgenes were inherited to the progeny without Mendelian segregation.

Figure 3:
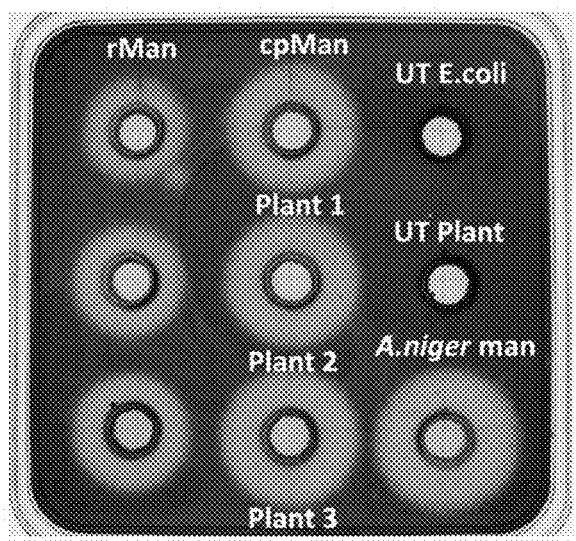
FIG. 3 Gel diffusion assay for mannanase activity. Agar plate with 0.1% locust bean gum substrate stained with Congo red dye to evaluate mannanase activity. 100 µg of rMan, E. coli-derived mannanase crude extract; 100 µg of cpMan, leaf extract from different transplastomic plant lines (Plant 1, 2 & 3); UT E. coli, Untransformed E. coli extract; UT plant, Untransformed plant extract; A. niger man, purified Aspergillus niger mannanase (Megazyme).

Evaluation of chloroplast-derived mannanase enzyme activity Qualitative gel diffusion assay using congo red dye was performed in order to assess the enzyme activity of chloroplast-derived mannanase (cpMan) and E. coli-derived mannanase (rMan). The mannanase enzyme breaks down the polymeric galactomannan substrate, reducing the binding of congo red dye and consequently generates a clearing zone. Both cpMan and rMan showed visible zone of clearance around the wells indicating gel areas hydrolyzed by endo-β-mannanase activity (FIG. 3). Mannanase enzyme activity is directly proportional to the diameter of the zone of clearance. Moreover, the diameter of the clearing zone in cpMan was more than rMan when equal amount of protein crude extract (100 µg) was loaded in these wells indicating that cpMan was more active than rMan. No clearing zone was observed in untransformed plant extract and E. coli harboring pLD vector (without man1 gene, FIG. 3). Circular area hydrolyzed by commercial purified mannanase (endo-β-mannanase from *Aspergillus niger*, Megazyme) was also clearly visible surrounding the well. Furthermore, in blank wells without the substrate, none of the extracts showed any clearing zone or non specific activity.

Characterization of Chloroplast-Derived and E. coli-Derived Mannanase

Figure 4:
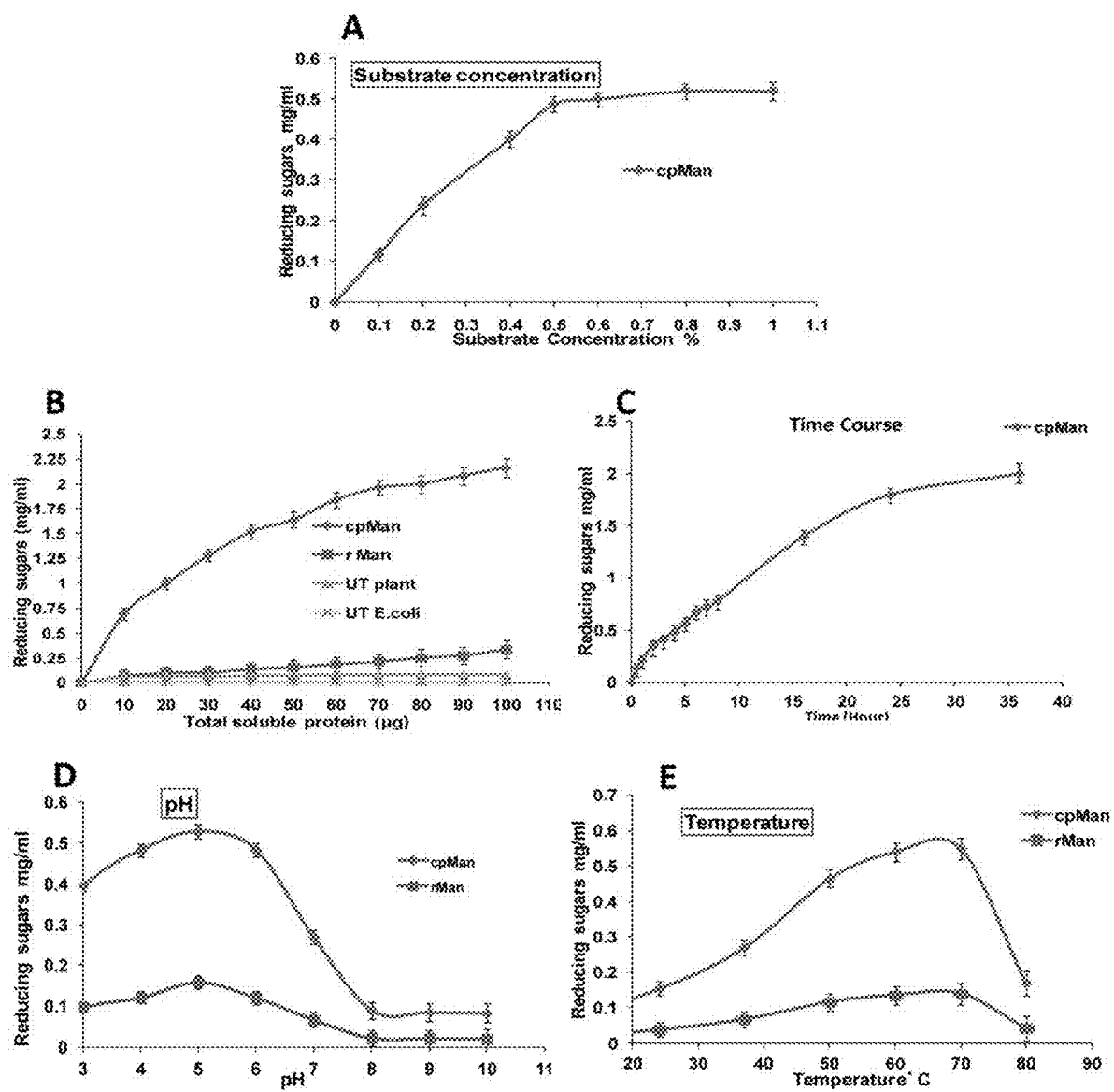
FIG. 4 Characterization of chloroplast-derived mannanase. A, Substrate Locust bean gum (0.5%) incubated with crude enzyme extracts in increasing concentrations of total soluble protein at 70° C., pH 5.0 in a reaction for 16 hours. B, Effect of increasing locust bean gum concentration on cpMan activity. C, Effect of incubation time on cpMan activity. D, Effect of pH on cpMan and rMan activity. E, Effect of temperature on cpMan and rMan activity. 30 µg of total soluble protein was incubated with 0.5% of locust bean gum at indicated reaction parameters for 2 hrs. rMan, E. coli-derived mannanase crude extract; cpMan, leaf extract from transplastomic plants; UT E. coli, Untransformed E. coli extract; UT plant, untransformed plant extract. (Error bars indicates the standard deviation; n=3)

Since chloroplast promoters function efficiently in E. coli, crude extract from E. coli harboring pLDman1 was used for quantitative comparison of enzyme activity with chloroplast-derived enzyme. Enzyme assays were performed using locust bean gum (galactomannan) as the substrate. Both plant and E. coli extract showed optimal activity at 0.5% locust bean gum and reducing sugars increased at a directly proportional rate until this concentration was reached (FIG. 4A). Hence, all subsequent enzyme characterization studies were carried out at this substrate concentration. Both cpMan and rMan released more reducing sugars with increasing protein concentration. However, chloroplast-derived mannanase released more reducing sugars at all of the tested total soluble protein (TSP) concentrations when compared to the E. coli-derived mannanase (FIG. 4B). This data shows that the chloroplast expression system is more efficient up to 6-7 folds higher at 100 µg TSP than the bacterial system. Untransformed plant extract and E. coli did not yield any significant amount of reducing sugars under standard assay conditions. The primary purpose of this study was to use the plant crude extract without purification for lignocellulosic biomass hydrolysis in order to make the process cost effective. Time dependent changes in enzyme activity of cpMan showed a linear increase in release of reducing sugars with increasing time. The cpMan continued to increase enzyme activity even up to 36 hours of incubation indicating stability of this enzyme for long durations at 70° C. (FIG. 4C).

The primary purpose of this study was to use crude extracts of chloroplast-derived mannanase along with the other chloroplast-derived enzymes in a cocktail for hydrolysis of lignocellulosic biomass. Temperature and pH are important characteristics for efficient use of crude enzyme extracts in cocktails. Crude enzyme extract (30 µg TSP) from plant and E. coli harboring mannanase expression cassette was used to study the effect of pH and temperature on mannanase activity using the locust bean gum (0.5%) as substrate. The optimal pH for cpMan and rMan under the standard assay conditions was pH 5.0. The pH stability curve showed that cpMan retained >50% of its maximal activity within a broad pH range from pH 3 to pH 7, whereas rMan retained only 42% within this range. However, at pH 8, both cpMan and rMan lost more than 80% of its activity (FIG. 4D). These data suggest that mannanase enzyme was more active in the acidic pH range. The optimal temperature for cpMan and rMan was 70° C. under the standard assay conditions. The enzyme activity increased with increase in temperature up to 70° C. in both *E. coli* and chloroplast-derived mannanase as indicated by the temperature stability curve. Further rise in temperature affected enzyme activity drastically and about 70% of its activity was lost (FIG. 4E).

Young, mature and old leaves from transplastomic mannanase plants were collected and mannanase activity was measured using carob galactomannan as the substrate. One unit of mannanase activity is defined as the amount of enzyme which released one micromole of reducing-sugar equivalents per minute from low viscosity carob galactomannan (2 mg/ml) at pH 5.0 and under temperature 70° C. Maximum enzyme activity was observed in mature and old leaves (25 Units/g fresh weight) of transplastomic mannanase plants, where as young leaves showed 44% less activity (11 Units/g). No mannanase activity was detected in untransformed crude leaf extracts whereas *E. coli*-derived mannanase had 6-7 folds less activity when compared to chloroplast-derived mannanase at 100 μg TSP. Based on the observed expression levels, up to 2,366 units of mannanase can be harvested from each tobacco plant. With 8000 tobacco plants grown in one acre of land, 18 million units of mannanase can be produced per single cutting. Typically with 3 cuttings per year 56 million units of mannanase can be harvested per year. These results were obtained using an experimental variety of tobacco Petite Havana which gives about 2.2 tons biomass of fresh leaves. The commercial cultivar produces 20 times more biomass hence it is expected to provide 20 fold higher enzyme yield.

Enzyme Cocktail for Hydrolysis of Pinewood

Figure 5:
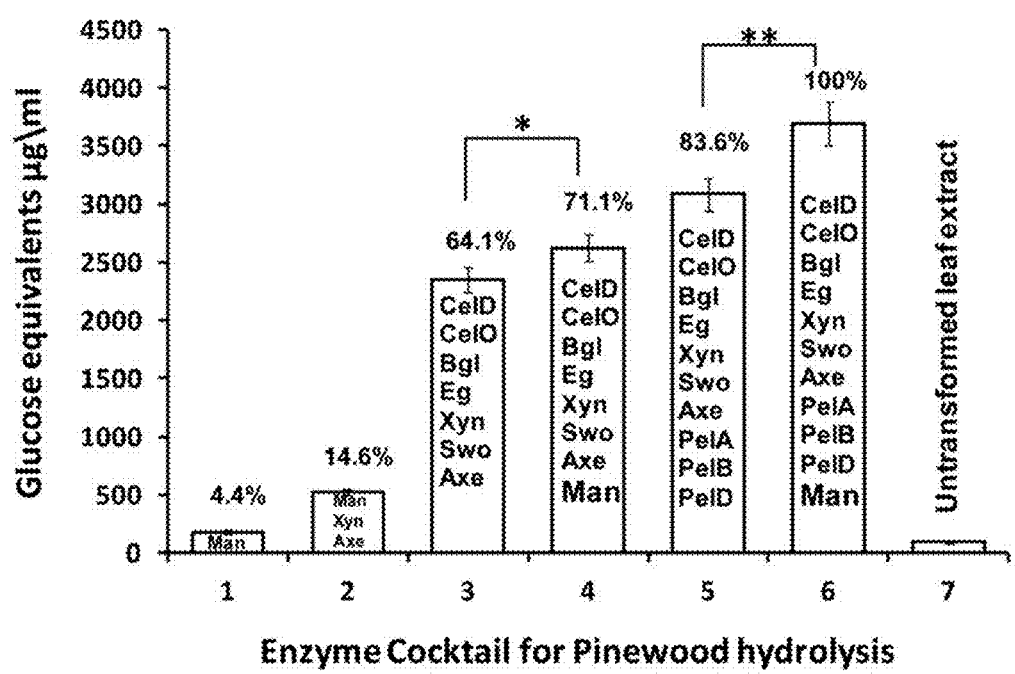
FIG. 5 Enzyme cocktail for pinewood hydrolysis. Pinewood (200 mg/5 ml) hydrolysis using different formulations of crude enzyme cocktails. Glucose equivalents released were quantified using DNS method. 200 ug TSP of crude chloroplast derived enzyme extracts were used. Man, Mannanase; Xyn, Xylanase; Axe, Acetyl xylan esterase; CelD, Endoglucanase; CelO, Exoglucanase; Bgl, β glucosidase; Eg1, Endoglucanase; Swo, Swollenin; Pel A, B, D, Pectate lyase. (Error bar indicates standard deviation among triplicates, * p value=0.038, ** p value=0.013, p value were calculated using t-test)

Chloroplast-derived enzymes were used in different formulations to make various cocktails for hydrolysis of pinewood. Chloroplast-derived mannanase (Man) alone showed 4.4% of the total hydrolysis of pinewood (FIG. 5, bar 1). The hydrolysis was further increased up to 14.6% when mannanase was mixed with xylanase (Xyn) and acetyl xylan esterase (Axe; FIG. 5, bar 2). When we used Xyn and Axe along with endoglucanases (CelD, Eg1), exoglucanase (CelO) and swollenin (Swo), the hydrolysis increased up to 64.1% (FIG. 5, bar 3). Supplementation of Man to this cocktail enhanced the hydrolysis by 11% attaining 70.1% of the total hydrolysis (FIG. 5, bar 4). Besides cellulose and hemicellulose, pectin is the core structural component of plant cell wall of woody plants which includes pine trees. Hydrolysis of pectin component should therefore increase the release of fermentable sugars by cellulases and hemicellulases. When we treated pinewood with pectate lyases (PelA, PelB, PelD) followed by supplementation with the enzyme cocktail in bar 3, the overall hydrolysis was extended up to 83.6% (FIG. 5, bar 5). Addition of mannanase to this cocktail boosted the hydrolysis to maximum amount resulting in liberation of 20% more glucose equivalents (FIG. 5, bar 6). Statistical analysis between cocktails with (FIG. 5, bar 4 and 6) or without mannanase (FIG. 5, bar 3 and 5) showed significant difference in release of fermentable sugars. Addition of leaf extract from untransformed plants to pinewood did not yield any measurable sugars (FIG. 5, bar 7). These results indicate that mannanase plays a significant role in efficient hydrolysis of pinewood biomass to release fermentable sugars.

Discussion of Examples

Lignocellulosic biomass is a heterogeneous complex of different polymers which is composed of intricate intertwined polymers. Therefore, concurrent presence of different classes of cell wall degrading enzymes that can disintegrate biomass and increase the access of each other to the complex structure of biomass is required for the efficient hydrolysis to obtain fermentable sugars. Thus, a mixture of enzymes such as cellulases, hemicellulases including mannanases, ligninases and accessory enzymes like lipases, pectate lyases, esterases may be required depending upon the composition of the biomass [3]. In the foregoing examples, fungal mannanase was expressed in tobacco chloroplasts. To our knowledge, this is the first report of over expression of fungal mannanase in plants and its direct utilization in enzyme cocktails for lignocellulosic biomass hydrolysis. For production of mannanase, tobacco lines harboring man1 gene from *Trichoderma reesei* were generated. Site specific integration of mannanase gene in chloroplast genome was achieved by using transcriptionally active spacer region between the trnI and trnA genes for homologous recombination. This region has been consistently used for efficient transgene integration and has several unique advantages [32,46,47]. Used was the psbA promoter and 5' UTR to achieve high levels of expression. The endogenous psbA regulatory elements have been used for the creation of transplastomic tobacco plants with elevated expression levels for a large number of diverse proteins [32,33,45,48]. The transplastomic mannanase plants exhibited maternal inheritance. In most crop species, organelle genomes are maternally inherited thereby excluding plastid integrated transgenes from pollen transmission. During pollen development plastids are unequally distributed, localizing all plastids into vegetative cells and excluding generative cells. Hence, sperm cells which originate from generative cells lack plastids [34]. Therefore transplastomic tobacco plants lack Mendelian inheritance. Maternal inheritance of transgenes was demonstrated in transplastomic tobacco plants where only 6 out of 2.1 million seedlings showed paternal inheritance with a frequency of $2.86 \times 10^{-6}$ [49].

Carbohydrate binding molecule (CBM) plays an important role in binding of the enzyme to the carbohydrate substrate. Celluloytic enzymes when expressed in chloroplasts might cause their deleterious effect by sequestration or degradation of the intermediates of carbohydrate metabolism [41]. Mild phenotypic effects in mannanase transplastomic plants were observed which could be due to the presence of CBM in mannanase. Mannanase from *Trichoderma reesei* has been reported to contain a carbohydrate binding module, which increases its hydrolytic activity [24]. The observed phenotypic effect could also be due to the decreased chloroplast thylakoid lipid content in transplastomic plants expressing mannanase. Our preliminary studies showed decrease in MGDG and DGDG in transplastomic lines expressing mannanase (data not shown) and further investigations are in progress to understand the observed phenotype. An *Arabidopsis* mutant deficient in DGDG showed similar phenotype [50,51]. In the above examples, the psbA promoter from tobacco was used for hyper-expression. Use of a heterologous psbA promoter [32] or gene 10 regulatory elements [31] could lower the expression levels and produce mannanase plants without any phenotypic effects.

Qualitative gel diffusion assay with locust bean gum (galactomannan) substrate using congo red dye showed endo β mannanase activity in crude extracts of transplastomic mannanase plants and *E. coli*. Similar assay has been used for detection and quantification of endo β mannanase activity present in seeds, fruit, bulbs and fungi [52,53]. Congo red shows high specificity of binding for polysaccharides containing adjacent (1, 4) β-linked D-glucopyranosyl units and galactoglucomannans [54]. Endo mannanase activity lessens the oligomeric length and hence decreases binding of congo red dye. The assay is insensitive for exo-activity and therefore confirms specific endo mannanase activity. The action of mannanase therefore creates a clearing zone which is proportional to the enzyme concentration. This confirms that the crude leaf extract from transplastomic plants contains active mannanase. Since the 3D structure of mannanase consists of disulfide bonds, proper folding of the protein is important for a fully functional enzyme. Chloroplast-derived mannanase folded correctly and was fully functional. Lack of disulfide bond formation in E. coli might be the reason for the low activity of mannanase expressed in E. coli when compared to chloroplast-derived enzyme. Also in a recent study, inhibitors were identified in crude E. coli extracts because addition of E. coli crude extract to plant extracts significantly decreased the enzyme activity in the plant extracts [42]

In the current study, 25 units of mannanase were obtained per gram fresh weight of mature leaves harvested at 6 PM. Chloroplast-derived mannanase had 6-7 fold higher mannanase activity than E. coli mannanase. Higher activity (up to 24 fold) in chloroplast-derived biomass hydrolysis enzymes (CelO, EG1) when compared to those expressed in E. coli was reported previously [42]. Characterization of chloroplast expressed mannanase showed that the enzyme is biologically as active as the fungal counterpart in the pH range of pH 3.0 to 7.0 with the peak activity at pH 5.0. The optimal temperature for the chloroplast-derived enzyme was 70° C. Such high temperature appears to be common with fungal β mannanase [16,18,58]. As chloroplast expressed mannanase was functional in crude enzyme extracts derived from mannanase expressing plants, it can be directly added to an enzyme cocktail for biomass hydrolysis without the need for any purification eventually lowering the cost. According to NC state University Tobacco guide 2011, the cost of tobacco cultivation is $3169 per acre. Based on the observed expression levels of mannanase, about 56 million units of mannanase can be produced per acre per year of tobacco cultivation with the production cost as low as 0.005 cents per enzyme unit (as defined in the commercial source Megazyme). This cost is 6,000 fold less when compared with the commercial purified mannanase (Megazyme).

In softwood like pinewood, glucomannans are closely associated with cellulose microfibrils and are integrated into mass of cellulose. These glucomannans are arranged in parallel to cellulose fibrils and are tightly interconnected [6,59]. This structural arrangement could inhibit the access of cellulases to the cellulose fibrils. Further in a recent study, it was reported that mannan polysaccharides are masked by pectic homogalacturonan (HG) in the primary cell wall and the recognition of mannan epitopes was greatly increased by enzymatic removal of pectic HG by treatment with pectate lyases [60]. Such type of association indicated by the masking of mannans may have a structural role in maintaining primary cell wall integrity. Also, pectic HG may coat mannans and other hemicelluloses, and thus limit or control the access of enzymes to these polysaccharides [60]. Therefore for the efficient breakdown of softwood biomass an enzyme cocktail comprising of mannanase and other cellulolytic enzymes are required. In our study, when mannanase was added to two different cocktails (FIG. 5 bar 3 and bar 5) hydrolysis was enhanced significantly (FIG. 5 bar 4 and bar 6). This could be due to the hydrolysis of the mannans present in the pinewood resulting in loosening of the structural arrangement and increased access of cellu-lases, thereby resulting in enhanced glucose release. It is well known that carbohydrate binding module (CBM) binds to the carbohydrate increases the enzyme concentration at the substrate surface and augments the effectiveness of enzyme [25].

Low cost production of mannanase would be highly beneficial for its diverse applications in the paper, oil, pharmaceutical, coffee and detergent industries. Expression of mannanase in plant chloroplasts is an important addition to the list of different cellulolytic enzymes expressed in chloroplast, which significantly enhances the release of fermentable sugars from the lignocellulosic biomass. This study reports the first successful expression of fungal mannanase in plants and its utilization in the release of fermentable sugars for bioethanol production.

Materials and Methods for Examples

Construction of Chloroplast Transformation Vector Harboring man1 Gene

Trichoderma reesei genomic DNA was obtained from ATCC and used as template for the amplification of three exons of mannanase gene (L25310) using sequence specific primers. Full length cDNA of mannanase was amplified from the exons by a PCR based method [43] using the forward of first exon flanked by NdeI restriction site and reverse of third exon flanked by XbaI restriction site. Full length amplified product was ligated to pCR Blunt II Topo vector (Invitrogen) and checked for any PCR errors by DNA sequencing (Genewiz). Mannanase coding sequence was excised from Topo vector by double digestion with NdeI and XbaI and inserted into the pLD vector [36,42,45] to create the tobacco chloroplast expression vector. The final clone was designated as pLD-man1.

Generation of Transplastomic Tobacco Plants

Nicotiana tabacum var. Petite Havana was grown aseptically on Murashige and Skoog medium containing 30 gm/l sucrose. Sterile young leaves from plants at 4-6 leaf stages were bombarded using gold particles coated with plasmid DNA of chloroplast transformation vector pLD-man1 using Bio-Rad PDS-1000/He particle delivery system as described earlier [45,46]. Bombarded leaves were kept in dark for 48 hours, cut into small pieces and then placed on RMOP regeneration media containing 500 mg/l spectinomycin for selection of transformants [45,46]. Putative transplastomic shoots emerged in 4-6 weeks after selection.

Confirmation of Site Specific Integration of Transgenes by PCR Analysis

Putative transplastomic shoots were screened by PCR for transgene integration. Total plant DNA was extracted from the putative transplastomic shoots using Qiagen DNeasy Plant mini kit following manufacturers' protocol and used as template for PCR analysis. To verify the site specific integration of the transgene cassette into the trnI/trnA inverted repeat region of chloroplast genome, PCR was carried out using the primer sets 3P-3M (3P-5'-AAAACCCGTCCTCA-GTTCGGATTGC-3' (SEQ ID NO: 1) and 3M-) and 5P-2M (5P-5'CCGCGTTGTTTCATCAAGCCTTACG-3' (SEQ ID NO: 2) and 2M-5'-TGACTGCCCACCTGAGAGCG-GACA-3' (SEQ ID NO: 3)) as described earlier [36,45]. Primer 3P anneals to the native chloroplast genome upstream of the site of integration and primer 3M is complimentary to the aadA gene. Primer 5P anneals with the aadA gene whereas primer 2M is complimentary to the trnA gene. PCR amplification was carried out using following program—Initial denaturation at 94° C. for 5 minutes; 30 cycles of 94° C. for 1 minute, 56° C. for 1 minute, 72° C. for 3 minutes; final extension at 72° C. for 10 minutes [45]. Amplified products were analyzed by agarose gel electrophoresis. After the confirmation of site specific integration of transgene cassette, leaves were cut into small pieces and placed on RMOP media containing spectinomycin 500 mg/l for second round of selection. Subsequently, the regenerated shoots were rooted on half strength MS medium containing spectinomycin 500 mg/l for third round of selection and evaluated for homoplasmy by Southern blot.

Confirmation of Homoplasmy by Southern Blot Analysis

Total plant genomic DNA was isolated from PCR confirmed shoots and digested completely with ApaI (NEB) enzyme. The digested DNA was separated on 0.8% agarose gel and placed in depurination solution (0.25 N HCl) for 15 minutes followed by two washes with double distilled water for 5 minutes each. The gel was then soaked in transfer buffer (0.4 N NaOH, 1 M NaCl) for 20 minutes and blotted onto the nylon membrane. The membrane was rinsed twice in 2×SSC (0.3 M NaCl and 0.03 M Sodium citrate) and the DNA was cross linked to the membrane using GS Gene linker UV chamber. The 0.81 kb flanking sequence for probe was generated by double digestion of pUC-Ct vector with BamHI and BglII. The mannanase exon1 DNA fragment was amplified and used for gene specific probe preparation. The DNA fragments for probe were labeled with $^{32}P$ α [dCTP] using Ready-to-go DNA labeling beads (GE) following manufacturer's protocol. The membrane was hybridized with the labeled probe using Stratagene Quick-HYB hybridization solution following manufacturer's instructions. After hybridization, the membrane was exposed overnight to X-ray film with an intensifying screen at −80° C. and then developed to visualize the autoradiographic signal to confirm homoplasmy. The homoplasmic shoots were transferred to autotrophic medium, kept in high humidity for 2 weeks and then transferred to the green house as described earlier [45]. Transplastomic seeds were surface sterilized and placed on half strength MSO medium containing spectinomycin (500 mg/L) along with untransformed seeds.

Crude Enzyme Preparation from *E. coli*

*E. coli* cells (XL-10 gold) harboring pLD-man1 vector and pLD vector (without man1 gene) were grown overnight at 37° C. in LB media containing 50 mg/l ampicillin. The cells were collected by centrifugation at 8,000 rpm under cold conditions and washed with 50 mM sodium citrate buffer (pH 5.0). The cells were finally suspended in 3 ml of 50 mM sodium citrate buffer (pH 5.0) containing protease inhibitor cocktail (Roche) followed by 5 sonication pulses of 30 seconds each with pause time of 30 seconds between the pulses. The supernatant was collected by centrifuging the lysate at 10,000 rpm under cold conditions and used as crude *E. coli* enzyme extract in the functional assays. Protein concentration in the extract was quantified using Biorad protein assay kit (BIO-RAD) based on the method of Bradford following manufacturer's protocol.

Enzyme Preparation from Transplastomic Tobacco Leaves

Fresh leaves were harvested from green house grown transplastomic mannanase plants along with untransformed plants and were ground in liquid nitrogen. The ground material was suspended in 50 mM sodium citrate buffer (pH 5.0) containing protease inhibitor cocktail (Roche) and vortexed at 4° C. for 15 minutes. The supernatant was collected by centrifugation at 10,000 rpm under cold conditions. The extract was filtered through 0.2 µm syringe filter followed by Amicon Ultra centrifugal filter unit-4 (10,000 NMWL) to remove the sugars present in the extract. This extract was used as crude plant enzyme extract for functional assays. Protein concentration was determined (mg/ml) using Biorad protein assay kit (BIO-RAD) based on the method of Bradford following manufacturer's protocol.

Mannanase Gel Diffusion Assay

Gel diffusion assay was performed to evaluate the mannanase activity of chloroplast-derived (cpMan) and *E. coli*-derived (rMan) using locust bean gum (Sigma G0753). Locust bean gum is galactomannan extracted from seeds of *Ciratonia siliqua*. Locust bean gum (0.1%) was suspended in 50 mM sodium citrate buffer pH 5.0 by boiling while constantly stirring. The mixture was centrifuged at 3,000 rpm and the supernatant was collected. Phytagel (0.7% w/v) was dissolved in this mixture by heating. The contents were then poured into plates and were allowed to set. Wells were punctured into the gel plates. Crude enzyme extract cpMan and rMan (100 µg) were added into the wells along with *Aspergillus niger* mannanase (Megazyme) as positive control, whereas protein extract from untransformed plant and *E. coli* harboring pLD vector (without man1 gene) as negative controls. The plates were incubated at 37° C. for 16 hours. These plates were then shaken gently for 15 minutes after adding Congo red dye (1% w/v) and washed with 1 M NaCl until the wells were transparent [52]. The zone of clearance showing mannanase activity was investigated.

Determination of Optimal Substrate Concentration, pH and Temperature for Mannanase Activity Optimal substrate concentration was determined by using different concentrations of locust bean gum substrate ranging from 0.1% to 1% in a reaction containing 30 µg TSP of cpMan. The effect of temperature on mannanase activity was investigated by incubating 30 µg TSP of cpMan and rMan with 0.5% locust bean gum (pH 5.0) at different temperatures of 24, 37, 50, 60, 70, 80° C. For evaluation of the optimal pH, a reaction with 30 µg TSP of cpMan and rMan with 0.5% of substrate was setup in sodium citrate buffer (pH 3.0, 4.0, 5.0 and 6.0), phosphate buffer (pH 7.0 and 8.0) and Tris-HCl buffer (pH 9.0 and 10.0) at 70° C. for 2 hours. To determine the stability of cpMan for longer duration, reactions were set with 0.5% substrate containing 30 µg TSP of cpMan at 70° C. for different time points ranging from 30 minutes to 36 hours.

Mannanase Enzyme Activity Assay

Mannanase enzyme activity assay was performed using locust bean gum as substrate. The substrate was suspended in 50 mM Sodium citrate buffer pH 5.0 and heated until boiling while stirring continuously. The substrate was cooled and allowed to homogenize while stirring overnight. The insoluble material was removed by centrifugation [16] and supernatant was used as substrate for the reaction. Increasing concentration of total soluble protein (TSP, 10 µg to 100 µg) from cpMan and rMan were taken in a 500 µl reaction containing 0.5% locust bean gum substrate in 50 mM Sodium citrate buffer pH 5.0 at 70° C. for 16 hours. BSA (100 µg/ml) was added to all reactions. Protein extract from untransformed plant and *E. coli* harboring pLD vector (without man1 gene) were used as negative controls. The reducing sugars released after the reaction were quantified by DNS method taking appropriate dilutions of the reaction samples. Absorbance was read at 540 nm and mannose was used as standard to measure the reducing sugars liberated after the reaction [61]. For mannanase unit calculation, carob galactomannan (Megazyme) was used as substrate. Mannanase activity in plants was quantified by comparison with enzyme activity of commercially available mannanase (Megazyme E-BMANN). One unit of mannanase activity is defined as the amount of enzyme which released one micromole of reducing-sugar equivalents per minute from low viscosity carob galactomannan (2 mg/ml, pH 5.0, and 70°

C.). All experiments had appropriate controls containing substrate without enzyme or enzyme without substrate.

Hydrolysis of Pinewood with Chloroplast-Derived Enzymes

Dried pinewood sample (*Pinus ponderosa*) was obtained from KL Energy Corporation (Rapid City, S. Dak., USA). Pinewood hydrolysis was carried out as described earlier [42]. Crude enzyme extracts obtained from the tobacco plants expressing a variety of biomass degrading enzymes were used to make various formulations of enzyme cocktails for pinewood hydrolysis. Prior to hydrolysis reaction, pinewood biomass was washed several times in distilled water until there was no sugar detected in the sample by DNS method. The hydrolysis reaction was carried out at 40-50° C. for 36 hours in 50 mM sodium citrate buffer (pH 5.0), 5 mM $CaCl_2$ and 100 µg of BSA per 5 ml reaction containing 200 mg pinewood. Pinewood hydrolysis was done at 50° C. as other enzymes present in the cocktail were more active within the range of 40-60° C. Mannanase retained most of its activity at 50° C. The various cocktails were comprised of chloroplast-derived enzymes Mannanase (Man), Xylanase (Xyn gene from *Trichoderma reesei*), Cellulase (CelD gene from *Clostridium thermocellum*), Endoglucanase (Eg1 gene from *Trichoderma reesei*), Exoglucanase (CelO gene from *Clostridium thermocellum*), β glucosidase (Bgl gene from *Trichoderma reesei*), Pectate Lyases (Pel A, B, D genes from *Fusarium solani*), Acetyl xylan esterase (Axe1 gene from *Trichoderma reesei*) and Swollenin (Swo gene from *Trichoderma reesei*) [42]. The enzyme activity (units/mg) in crude total soluble protein of all chloroplast derived enzymes except mannanase was determined in earlier study [42]. In this study, for all cocktails, 200 µg TSP of each enzyme extract was used whereas negative control reaction contained 2000 µg TSP of untransformed leaf extract in 5 ml of hydrolysis reaction. All the reactions were carried out in a rotary shaker at 150 rpm. End product fermentable sugars were determined by DNS method [61] with D-glucose as standard. The percent hydrolysis of pinewood by different cocktails was calculated based on considering maximum release of fermentable sugars as 100% hydrolysis. The "percent increase" among other cocktails was calculated based on the release of sugars. Ampicillin and kanamycin 100 µg/ml was supplemented to inhibit any microbial growth during the prolonged hours of enzyme hydrolysis. All experiments were carried out in triplicate and statistical analysis was performed using t-test.

CITED REFERENCES

1. Robertson G P, Dale V H, Doering O C, Hamburg S P, Melillo J M, et al. (2008) Sustainable biofuels redux. Science 322: 49-50
2. Yang B, Dai Z, Ding S, Wyman C E (2011) Enzymatic hydrolysis of cellulosic biomass, Biofuels, 2 (4), 421-450
3. Abramson M, Shoseyov O, Shani Z (2010) Plant cell wall reconstruction toward improved lignocellulosic production and processability. Plant Science 178: 61-72
4. Capek P, Kubackova M, Alfoldi J, Bilisics L, Liskova D and Kakoniova D (2000) Galactoglucomannan from the secondary cell wall of *Picea abies* L. Krast. Carbohydr Res 329: 635-645
5. Pereira H, Graca J, Rodrigues J C (2003) Wood chemistry in relation to quality. In: Barnett, J. R., Jeronimidis, G. (Eds.), Wood Quality and Its Biological Basis. Blackwell Publishing, Oxford, pp. 53-86
6. Pham T A, Berrin J G, Record E, To K A, Sigoillot J (2010) Hydrolysis of softwood by *Aspergillus* mannanase: Role of a carbohydrate-binding module. J Biotechnol 148: 163-170
7. J K N Jones (1950) The structure of the mannan present in *Porphyra umbilicalis*. J. Chem. Soc. 3292-3295
8. Dunn E K, Shoue D A, Huang X, Kline R E, Mackay A L, et al. (2007) Spectroscopic and biochemical analysis of regions of the cell wall of the unicellular 'mannan-weed', Acetabulariaacetabulum. Plant Cell Physiol. 48(1):122-33
9. Hannon M, Gimpel J, Tran M, Rasala B, Mayfield S. (2010) Biofuels from algae: challenges and potential. Biofuels 1(5):763-784
10. Dhawan and Kaur (2007) Microbial mannanases: An overview of production and applications. Crit. Rev Biotechnol 27: 197-216
11. Moreira L R S and Filho E X F (2008) An overview of mannan structure and mannan-degrading enzyme systems. Appl Microbiol Biotechnol 79:165-178
12. Van Zyl W H, Rose S, Trollope K, Gorgens J (2010) Fungal β mannanases: Mannan hydrolysis, heterologous production and biotechnological applications. Process Biochemistry 45: 1203-1213
13. Jorgensen H, Sanadi A. R, Felby C, Lange N, Fischer M, et al. (2010) Production of Ethanol and Feed by High Dry Matter Hydrolysis and Fermentation of Palm Kernel Press Cake. Appl Biochem Biotechnol 161: 318-332
14. Banerjee G, Car S, Scott-Craig J S, Borrusch M, S, Walton J D (2010) Rapid optimization of enzyme mixtures for deconstruction of diverse pretreatment/biomass feedstock combinations. Biotechnol Biofuels 3: 22
15. Sun Y M, Yu H Y, Wang W J, Yang Y S, Yang Y H (2003) Purification and properties of *Bacillus subtilis* SA-22 endo-1,4-beta-D-mannanase. Sheng Wu Gong Cheng Xue Bao 19: 327-330
16. Stalbrand H, Siika-aho M, Tenkanen M, Viikari L (1993) Purification and characterization of two β-mannanases from *Trichoderma reesei*. J Biotechnol 29: 229-242
17. Ademark P, Varga A, Medve J, Harjunpaa V, Drakenberg T, et. al, (1998) Softwood hemicellulose-degrading enzymes from *Aspergillus niger* Purification and properties of a β-mannanase. J Biotechnol 63: 199-210
18. Arisan-Atac I, Hodits R, Kristufek D, Kubicek C P (1993) Purification and characterization of a β-mannanase of *Trichoderma reesei* C-30. Appl Microbiol Biotechnol 39: 58-62
19. Stalbrand H, Saloheimo A, Vehmaanpera J, Henrissat B, Penttila M (1995) Cloning and expression in *Saccharomyces cerevisiae* of a *Trichoderma reesei* β-mannanase gene containing a cellulose binding domain. Appl Environ Microbiol 61: 1090-1097
20. Sabini E, Schubert H, Murshudov G, Wilson K, Siika-Aho M, et al. (2000) The three dimensional structure of a *Trichoderma reesei* b-mannanase from glycoside hydrolase family 5. Acta Cryst D56: 3-13
21. Ratto M, Siika-aho M, Buchert J, Valkeajarvi A, Viikari L (1993) Enzymatic hydrolysis of isolated and fibre-bound galactomannans from pine-wood and pine kraft pulp. Appl Microbiol Biotechnol 40: 449-454
22. Tenkanen M, Makkonen M, Perttula M, Viikari L, Teleman A (1997) Action of *Trichoderma reesei* mannanase on galactoglucomannan in pine kraft pulp. J Biotechnol 57: 191-204

23. Oksanen T, Pere P, Paavilainen L, Buchert J, Viikari L (2000) Treatment of recycled kraft pulps with *Trichoderma reesei* hemicellulases and cellulases. J Biotechnol 78: 39-48
24. Hagglund P, Eriksson T, Cohen A, Nerinckx W, Claeyssens M, et al. (2003) A cellulose-binding module of the *Trichoderma reesei* β-mannanase Man5A increases the mannan-hydrolysis of complex substrates. J Biotechnol 101: 37-48
25. Guillen D, Sanchez S & Sanoja R (2010) Carbohydrate-binding domains: multiplicity of biological roles. Appl Microbiol Biotechnol 85: 1241-1249
26. Taylor II L E, Dai Z, Decker S R, Brunecky R, Adney W S, Ding S Y, Himmel M E (2008) Heterologous expression of glycosyl hydrolases in planta: a new departure for biofuels. Trends Biotechnol 26: 413-424
27. M. Sainz (2009) Commercial cellulosic ethanol: the role of plant-expressed enzymes. In Vitro Cell. Dev. Biol.-Plant, 45, pp. 314-329.
28. Cramer, C. L., J. G. Boothe, and K. K. Oishi. 1999. Transgenic plants for therapeutic proteins: linking upstream and down stream strategies. Curr. Top. Microbiol. Immunol. 240:95-118.
29. Sticklen M B (2006) Plant genetic engineering to improve biomass characteristics for biofuels Curr Opin Biotechnol. 17:315-319.
30. Oraby H, Venkatesh B, Dale B, Ahmad R, Ransom C, Oehmke J, et al. (2007) Enhanced conversion of plant biomass into glucose using transgenic rice-produced endoglucanase for cellulosic ethanol. Transgenic Res. 16(6):739-49
31. Verma D and Daniell H (2007) Chloroplast vector systems for biotechnology applications. Plant Physiol 145: 1129-1143
32. Ruhlman T, Verma D, Samson N, Daniell H (2010) The role of heterologous chloroplast sequence elements in transgene integration and expression. Plant Physiol 152: 2088-2104
33. Bally J, Nadai M, Vitel, M, Rolland, A, Dumain, R et al. (2009) Plant physiological adaptations to the massive foreign protein synthesis occurring in recombinant chloroplasts. Plant Physiol 150: 1474-1481
34. Daniell, H (2007) Transgene containment by maternal inheritance: effective or elusive? Proc Natl Acad Sci USA 104: 6879-6880
35. Bally J, Paget E, Droux M, Job C, Job D (2008) Both the stroma and thylakoid lumen of tobacco chloroplasts are competent for the formation of disulphide bonds in recombinant proteins. Plant Biotechnol J. 6 (1): 46-61
36. Daniell H, Lee S B, Panchal T, Wiebe P O (2001) Expression and assembly of the native cholera toxin B subunit gene as functional oligomers in transgenic tobacco chloroplasts. J Mol Bio 311: 1001-1009
37. Staub J M, Garcia B, Graves J, HajdukFiewicz P T J, Hunter P, et al (2000) High-yield production of a human therapeutic protein in tobacco chloroplasts. Nat Biotechnol 18: 333-338
33. Ruhlman T, Ahangari R, Devine A, Samsam M, Daniell H (2007) Expression of cholera toxin B-proinsulin fusion protein in lettuce and tobacco chloroplasts-oral administration protects against development of insulitis in non-obese diabetic mice. Plant Biotechnol J 5: 495-510
39. Ziegelhoffer T, Raasch J A, Austin-Phillips S (2009) Expression of *Acidothermus cellulolyticus* E1 endo-β-1, 4-glucanase catalytic domain in transplastomic tobacco. Plant Biotech J 7: 527-536
40. Jin S, Kanagaraj A, Verma D, Lange T, Daniell H (2011) Release of hormones from conjugates: chloroplast expression of β-glucosidase results in elevated phytohormone levels associated with significant Increase in biomass and protection from aphids or whiteflies conferred by sucrose esters (2011) Plant Physiol 155: 222-235
41. Petersen K, Bock R (2011) High-level expression of a suite of thermostable cell wall-degrading enzymes from the chloroplast genome. Plant Mol Biol July; 76(3-5): 311-21
42. Verma D, Kanagaraj A, Shuangxia J, Singh N D, Kolattukudy P, et al. (2010) Chloroplast-derived enzyme cocktails hydrolyse lignocellulosic biomass and release fermentable sugars. Plant Biotechnol J 8: 332-350
43. An X, Lu J, Huang J, Zhang B, Liu D, Zhang X, Chen J, Zhou Y, Tong Y (2007) Rapid assembly of multiple-exon cDNA directly from genomic DNA. PLoS ONE 2: e1179
44. Daniell H, Datta R, Varma S, Gray S, Lee S B (1998) Containment of herbicide resistance through genetic engineering of the chloroplast genome. Nat Biotechnol 16: 345-348
45. Verma D, Samson N P, Koya V, Daniell H (2008) A protocol for expression of foreign genes in chloroplasts. Nat Protoc 3: 739-758
46. Daniell H, Ruiz O N, Dhingra A (2004) Chloroplast genetic engineering to improve agronomic traits. Methods Mol. Biol. 286: 111-138
47. DeCosa B, Moar W, Lee S B, Miller M, Daniell H (2001) Overexpression of the Bt cry2Aa2 operon in chloroplasts leads to formation of insecticidal crystals. Nat Biotechnol 19: 71-74
48. Singh N D, Li M, Lee S B, Schnell D and Daniell H (2008) *Arabidopsis* Tic40 expression in tobacco chloroplasts results in massive proliferation of the inner envelope membrane and upregulation of associated proteins. Plant Cell 20: 3405-3417
49. Ruf S, Karcher D, Bock R (2007) Determining the transgene containment level provided by chloroplast transformation. Proc Natl Acad Sci USA 104: 6998-7002
50. Dormann P, Benning S, Balbo I, Benning C (1995) Isolation and Characterization of an *Arabidopsis* Mutant Deficient in the Thylakoid Lipid Digalactosyl Diacylglycerol The Plant Cell 7: 1801-1810
51. Klaus D, Hartel H, Fitzpatrick L M, Froehlich J E, Hubert J et al. (2002) Digalactosyldiacylglycerol Synthesis in Chloroplasts of the *Arabidopsis* dgd1 Mutant. Plant Physiol 128: 885-895
52. Downie B, Hilhorst H, Bewley D (1994) A new assay for quantifying endo-β-D-mannanase activity using congo red dye. Phytochemistry 36: 829-835
53. Still D W, Dahal P, Bradford K J (1997) A single-seed assay for endo-β-mannanase activity from tomato endosperm and radicle tissues. Plant Physiol 113: 13-20
54. Wood P J (1980) Specificity in the interaction of direct dyes with polysaccharides. Carbohydr Res 85: 271-287
55. Arlen P A, Falconer R, Cherukumilli S, Cole A, Cole A M, et al. (2007) Field production and functional evaluation of chloroplast-derived interferon-alpha2b. Plant Biotechnol J. 5(4):511-25
56. Glenz K, Bouchon B, Stehle T, Wallich R, Simon M M, Warzecha H (2006) Production of a recombinant bacterial lipoprotein in higher plant chloroplasts. Nat Biotechnol 24: 76-77
57. Boyhan D, Daniell H (2011) Low-cost production of proinsulin in tobacco and lettuce chloroplasts for injectable or oral delivery of functional insulin and C-peptide. Plant Biotechnol J 9: 585-598
58. Christgau S, Kauppinen S, Vind J, Kofod V, Dalboge H (1994) Expression, cloning, purification and characterization of a beta-1,4-mannanase from *Aspergillus aculeatus*. Biochem Mol Biol Int 33: 917-925
59. Salmen L (2004) Micromechanical understanding of the cell-wall structure. C R Biol 327: 873-880
60. Marcus S E, Blake A W, Benians T A S, Lee K J D, Poyser C, et al. (2010) Restricted access of proteins to mannan polysaccharides in intact plant cell walls. Plant J 64:191-203
61. Miller G L (1959) Use of Dinitrosalicylic acid reagent for determination of reducing sugar. Anal Chem 31:426-42

For background on expression of plant degrading materials, WO 2009/108941 is cited by reference.

It should be borne in mind that all patents, patent applications, patent publications, technical publications, scientific publications, and other references referenced herein and in the accompanying appendices are hereby incorporated by reference in this application to the extent not inconsistent with the teachings herein.

It is important to an understanding of the present invention to note that all technical and scientific terms used herein, unless defined herein, are intended to have the same meaning as commonly understood by one of ordinary skill in the art. The techniques employed herein are also those that are known to one of ordinary skill in the art, unless stated otherwise. For purposes of more clearly facilitating an understanding the invention as disclosed and claimed herein, the following definitions are provided.

While a number of embodiments of the present invention have been shown and described herein in the present context, such embodiments are provided by way of example only, and not of limitation. Numerous variations, changes and substitutions will occur to those skilled in the art without materially departing from the invention herein. For example, the present invention need not be limited to best mode disclosed herein, since other applications can equally benefit from the teachings of the present invention. Also, in the claims, means-plus-function and step-plus-function clauses are intended to cover the structures and acts, respectively, described herein as performing the recited function and not only structural equivalents or act equivalents, but also equivalent structures or equivalent acts, respectively. Accordingly, all such modifications are intended to be included within the scope of this invention as defined in the following claims, in accordance with relevant law as to their interpretation.

What is claimed is:

1. A method for producing plant degrading cocktail consisting of extracts of chloroplast produced β-mannanase, xylanase encoded by sequences obtained from *Trichoderma reesei*, acetyl xylan esterase encoded by sequences obtained from *Trichoderma reesei*, recombinant CelD endoglucanase encoded by sequences obtained from *Clostridium* termocellum, Eg1 endoglucanase, CelO exoglucanase encoded by sequences obtained from *Clostridium thermocellum*, recombinant Beta glucosidase encoded by sequences obtained from *Trichoderma reesei*, PelA pectate lyase, recombinant PelB pectate lyase encoded by sequences obtained from *Fusarium solani*, and PelD pectate lyase encoded by sequences obtained from *Fusarium solani* plant degrading enzymes and swollenin encoded by sequences obtained from *Trichoderma reesei*, wherein nucleic acids encoding said plant degrading enzymes and swollenin are introduced into chloroplasts of at least one plant, thereby producing transplastomic plants; said method comprising
   a) grinding said transplastomic plants in liquid nitrogen;
   b) suspending ground transplastomic plant material of step a) in a buffer in the presence of a protease inhibitor cocktail, thereby forming a suspension;
   c) subjecting said suspension to centrifugation and harvesting said enzymes in the resultant supernatant; and
   d) filtering said supernatant to remove any sugars present, thereby producing a crude plant enzyme extract for said plant degrading cocktail.

2. The method of claim 1, wherein said plant is tobacco.

3. A plant degrading enzyme cocktail useful in digesting a wood-based biomass sample consisting of extracts of chloroplast expressed degrading enzymes β-Mannanase, xylanase encoded by sequences obtained from *Trichoderma reesei*, acetyl xylan esterase encoded by sequences obtained from *Trichoderma reesei*, CelD endoglucanase encoded by sequences obtained from *Clostridium* termocellum, Eg1 endoglucanase encoded by sequences obtained from *Trichoderma ressei*, recombinant beta-glucosidase encoded by sequences obtained from *Trichoderma reesei*, CelO exoglucanase encoded by sequences obtained from *Clostridium thermocellum*, swollenin encoded by sequences obtained from *Trichoderma reesei*, PelA pectate lyase, PelB pectate lyase, and PelD pectate lyase or consisting of chloroplast produced β-Mannanase, xylanase, acetyl xylan esterase encoded by sequences obtained from *Trichoderma reesei*, CelD endoglucanase encoded by sequences obtained from *Clostridium* termocellum, Eg1 endoglucanase encoded by sequences obtained from *Trichoderma ressei*, CelO exoglucanase encoded by sequences obtained from *Clostridium thermocellum*, swollenin encoded by sequences obtained from *Trichoderma reesei*, recombinant PelA, and PelB pectate lyase encoded by sequences obtained from *Fusarium solani*, PelD pectate lyase, cellulase, recombinant beta-glucosidase encoded by sequences obtained from *Trichoderma reesei*, recombinant alpha amylase encoded by sequences obtained from *Bacillus* ssp., amyloglucosidase, and rubisco, said cocktail being effective to hydrolyze 100% of a wood biomass sample.

4. A method of producing the plant degrading enzyme cocktail of claim 3 comprising the steps of producing plants comprising chloroplasts that express said plant degrading enzymes, harvesting said plant; and processing said plant to produce plant degrading material suitable for mixing with and degrading a biomass sample.

5. The method of claim 3, wherein said wood-based biomass sample is pinewood.

6. The method of claim 3, wherein said extracts are in powdered form.

* * * * *

SEQUENCE LISTING

```
<160> NUMBER OF SEQ ID NOS: 3

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
aaaacccgtc ctcagttcgg attgc                                          25

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ccgcgttgtt tcatcaagcc ttacg                                          25

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tgactgccca cctgagagcg gaca                                           24
```